(12) United States Patent
Sayre et al.

(10) Patent No.: US 10,809,976 B2
(45) Date of Patent: *Oct. 20, 2020

(54) ATHLETIC PERFORMANCE DATA SYSTEM AND METHOD

(71) Applicant: NIKE, Inc., Beaverton, OR (US)

(72) Inventors: Matt Sayre, Portland, OR (US); Ken Black, Tigard, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/678,142

(22) Filed: Nov. 8, 2019

(65) Prior Publication Data

US 2020/0073630 A1  Mar. 5, 2020

Related U.S. Application Data

(63) Continuation of application No. 15/676,448, filed on Aug. 14, 2017, now Pat. No. 10,481,868, which is a continuation of application No. 14/048,755, filed on Oct. 8, 2013, now Pat. No. 9,733,898, which is a continuation of application No. 11/762,675, filed on Jun. 13, 2007, now Pat. No. 8,554,512.

(60) Provisional application No. 60/813,128, filed on Jun. 13, 2006.

(51) Int. Cl.
| | |
|---|---|
| *G06F 7/00* | (2006.01) |
| *A63B 71/06* | (2006.01) |
| *G06Q 50/22* | (2018.01) |
| *G16H 10/20* | (2018.01) |

(52) U.S. Cl.
CPC ............ *G06F 7/00* (2013.01); *A63B 71/06* (2013.01); *G06Q 50/22* (2013.01); *A63B 2225/15* (2013.01); *A63B 2225/20* (2013.01); *A63B 2225/50* (2013.01); *G16H 10/20* (2018.01)

(58) Field of Classification Search
CPC . A63B 71/06; A63B 2225/15; A63B 2225/20; A63B 2225/50; G06F 7/00
See application file for complete search history.

(56) References Cited

U.S. PATENT DOCUMENTS

| | | | |
|---|---|---|---|
| 6,013,007 A | 1/2000 | Root et al. | |
| 6,585,622 B1 * | 7/2003 | Shum | A61B 5/0004 482/8 |
| 6,615,251 B1 * | 9/2003 | Klug | G06F 21/41 709/218 |
| 2001/0034734 A1 | 10/2001 | Whitley et al. | |
| 2004/0148342 A1 | 7/2004 | Cotte | |
| 2004/0209600 A1 | 10/2004 | Werner et al. | |
| 2007/0213126 A1 | 9/2007 | Deutsch et al. | |
| 2008/0200312 A1 | 8/2008 | Tagliabue | |

* cited by examiner

*Primary Examiner* — Mohamed Charioui
(74) *Attorney, Agent, or Firm* — Banner & Witcoff, Ltd.

(57) ABSTRACT

An athletic performance data system has an athletic field data collection system for obtaining athletic performance data and athlete identifying information for plural athletes at an athletic performance event. An athletic data host server receives the athletic performance test data and athlete identifying information from the athletic field data collection system, and the athletic performance data and athlete identifying information are posted to an athletic performance web site in a separate, personalized page for each of the plural athletes.

20 Claims, 5 Drawing Sheets

ATHLETIC PERFORMANCE DATA SYSTEM AND METHOD

CROSS-REFERENCE TO RELATED APPLICATIONS

This application is a continuation of U.S. patent application Ser. No. 15/676,448, filed Aug. 14, 2017, which is a continuation of Ser. No. 14/048,755, filed Oct. 8, 2013, issued as U.S. Pat. No. 9,733,898, which is a continuation of U.S. patent application Ser. No. 11/762,675, filed Jun. 13, 2007, issued as U.S. Pat. No. 8,554,512, which claims the benefit of U.S. Provisional Application No. 60/813,128, filed Jun. 13, 2006, each of which is incorporated by reference in its entirety for any and all non-limiting purposes.

BACKGROUND AND SUMMARY OF INVENTION

Speed, agility, reaction time, and power are some of the determining characteristics influencing the athleticism of an athlete. Accordingly, athletes strive to improve their athletic performance in these areas, and coaches and recruiters tend to seek those athletes that have the best set of these characteristics for the particular sport.

One method for evaluating and comparing athletes' athleticism involves having the athletes perform a common set of exercises and drills. Athletes that perform the exercises or drills more quickly and/or more accurately are usually considered to be better than those with slower or less accurate performance for the same exercise or drill. For example, "cone drills" are routinely used in training and evaluating athletes. In a typical "cone drill" the athlete must follow a pre-determined course between several marker cones and, in the process, execute a number of rapid direction changes, and/or switch from forward to backward or lateral running.

Previously, efforts to meaningfully compile and evaluate the timing and other information gathered from these exercises and drills had been limited. For example, while the fastest athlete from a group of athletes through a given drill may be determinable, these known systems do not allow that athlete to be meaningfully compared to athletes from all over the world that may not have participated in the exact same drill on the exact same day. However, a universal and objective athleticism rating system for accurately detecting and recording athletic performance has now been described in PCT application No. /US2005/040493 for Athleticism Rating and Performance Measuring Systems, assigned to SPARQ, Inc. of Portland, Oreg.

An aspect of such athleticism rating systems is the collection results from various athletic performance tests for each athlete and calculating an athleticism rating from the data. The performance test results are typically recorded manually for each athlete and are entered or uploaded as performance data to a computer, such as a web server, to have the athleticism rating calculated. Such manual handling of the performance test results is generally manageable for the relatively small numbers of athletes on an individual team or at some athletic camps. But for larger numbers of athletes or other participants, manual handling of the performance test results can be unwieldy and can introduce errors in the transcription of the data.

Accordingly, the present invention includes an athletic performance data system having an athletic field data collection system for obtaining athletic performance data and athlete identifying information for plural athletes at an athletic performance event. An athletic data host server receives the athletic performance test data and athlete identifying information from the athletic field data collection system, and the athletic performance data and athlete identifying information are posted to an athletic performance web site in a separate, personalized page for each of the plural athletes.

In one implementation, the present invention includes an athletic field data collection system that provides automated handling and uploading of athletic performance data, such as for use in calculating athleticism ratings. In one implementation, the athletic field data collection system is portable and self-powered to be operable in the outdoor field environment of many athletic activities. The system provides accurate and reliable identification of the performance data for each athlete, minimizes the manual handling of the data by performance evaluators, and provides prompt uploading of the data for calculation of an athleticism rating. In addition, the system may provide an athleticism rating for each athlete as a separate web page that can be personalized by the athlete.

Additional objects and advantages of the present invention will be apparent from the detailed description of the preferred embodiment thereof, which proceeds with reference to the accompanying drawings.

DETAILED DESCRIPTION

Figure 1:
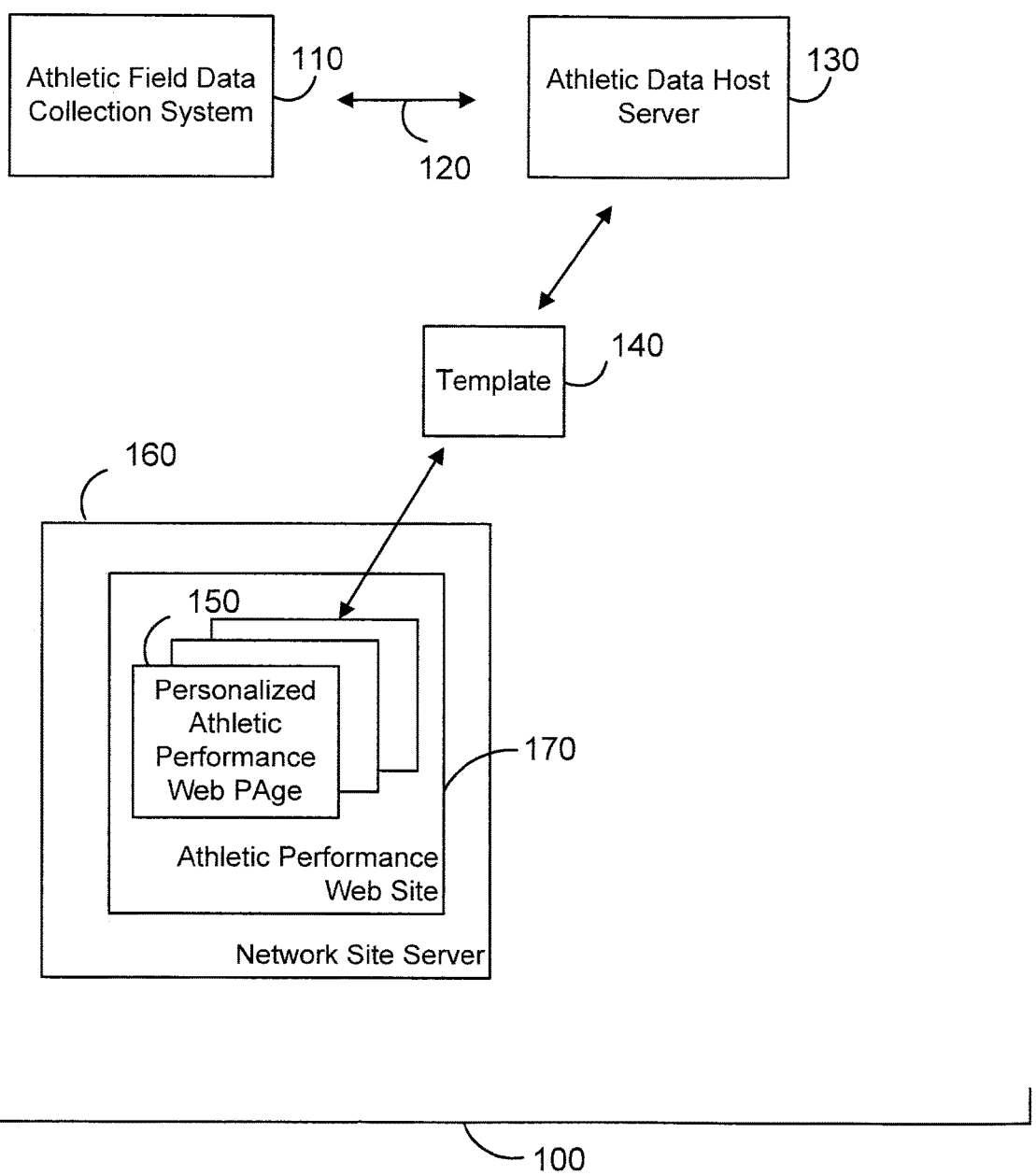
FIG. 1 is a block diagram of an athletic performance data system according to the present invention.

FIG. 1 is a block diagram of an athletic performance data system 100 according to the present invention. Athletic performance data system 100 includes an athletic field data collection system 110 that provides automated handling and uploading of athletic performance data, such as for use in calculating athleticism ratings. In one implementation, the athletic field data collection system 110 is portable and self-powered to be operable in the outdoor field environment of many athletic activities.

Athletic field data collection system 110 provides collection of data on athletic performance from numerous athletes performing a variety of athletic performance tests. For example, the athletic performance tests may form the basis of an athletic performance rating such as a universal and objective athleticism rating system for accurately detecting and recording athletic performance as described in PCT application No.

PCT/US2005/040493 for Athleticism Rating and Performance Measuring Systems, assigned to SPARQ, Inc. of Portland, Oreg. Such athletic performance tests may relate to general athletic fitness or performance or may relate to a specific sport.

Athletic field data collection system 110 transmits athletic performance test data and at least preliminary athlete identifying information via a communication channel 120 to an athletic data host server 130. Communication channel 120 may include a global computer network (e.g., the Internet) and a connection between it and athletic field data collection system 110. In one implementation, the connection between athletic field data collection system 110 and the global computer network may include a cellular telephone network connection to facilitate remote wireless communication.

Athletic data host server 130 receives the athletic performance test data and at least preliminary athlete identifying information for each participating athlete. The athletic performance test data and the athlete identifying information for each athlete are automatically entered into corresponding fields of a personalized athletic performance web page template 140. A personalized athletic performance web page 150 the incorporating the athletic performance test data and the athlete identifying information into template 140 is automatically posted to a network site server 160. In one implementation, athletic performance web page 150 forms part of an athletic performance web site 170 that is hosted on network site server 160 and has the personalized athletic performance web pages of multiple participating athletes.

In one implementation, each personalized athletic performance web page 150 automatically includes optional fields or segments into which the athlete may incorporate additional personal or other information to further personalize his or her athletic performance web page 150. Each personalized athletic performance web page 150 may be initially posted to athletic performance web site 170 in a private mode or a public mode. In the private mode the page 150 would be accessible only by the athlete, and in the public mode the page 150 would be accessible by generally anyone accessing the athletic performance web site. Even if initially posted in the private mode, the athlete could change the page 150 to be available in a public mode.

Figure 2:
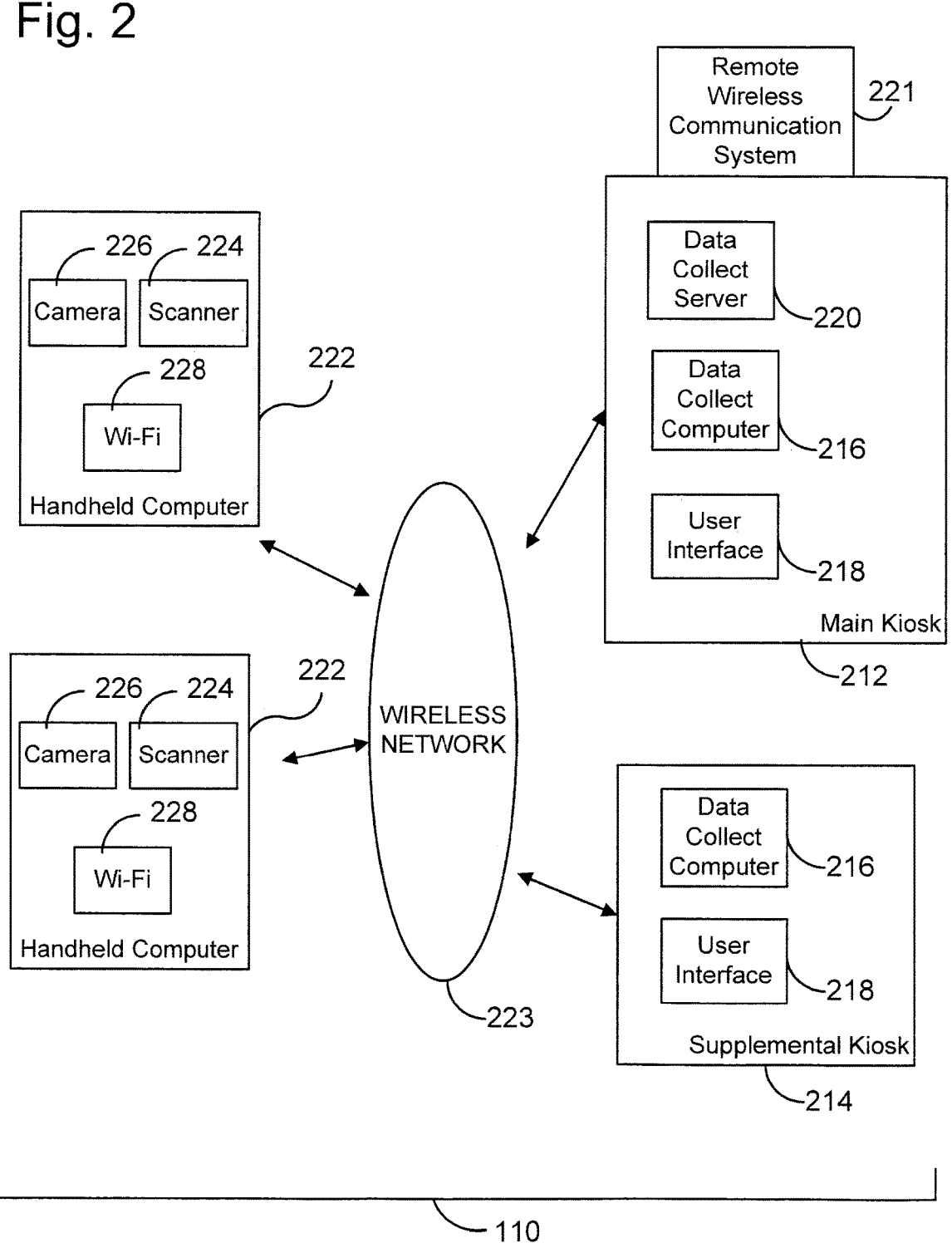
FIG. 2 is a block diagram of one implementation of an athletic field data collection system employed in the athletic performance data system of FIG. 1.

FIG. 2 is a block diagram of one implementation of an athletic field data collection system 110 employed in accordance with the present invention. Athletic field data collection system 110 includes a main data collection kiosk 212 and optionally one or more (e.g., three, only one shown) supplemental data collection kiosks 214. Each kiosk 212 and 214 is battery- or line-powered and includes a data collecting computer system 216 and a user interface (e.g., keyboard, touch screen, bar code scanner, etc.) 218 through which data can be entered into the data collecting computer system 216. Main data collection kiosk 212 also includes a data collection server 220 that is in wired communication with the data collecting computer system 216 in main kiosk 212 and communicates over a local wireless (e.g., wi-fi) network 223 with the data collecting computer systems 216 in supplemental kiosks 214. Main data collection kiosk 212 may further include a remote wireless communication system 221 for communicating over communication channel 120 with athletic data host server 130 (FIG. 1).

Data collection system 110 further includes one or more handheld computers 222 that each runs an athletic field data collection application to capture and store athletic performance results. In one implementation, each handheld computer 222 includes a barcode scanner 224, a digital camera 226 for taking athlete photos, and a wireless (e.g., wi-fi) interface 228 for wireless communication over local wireless (e.g., wi-fi) network 223 with data collection server 220 for transferring performance results thereto.

Figure 3:
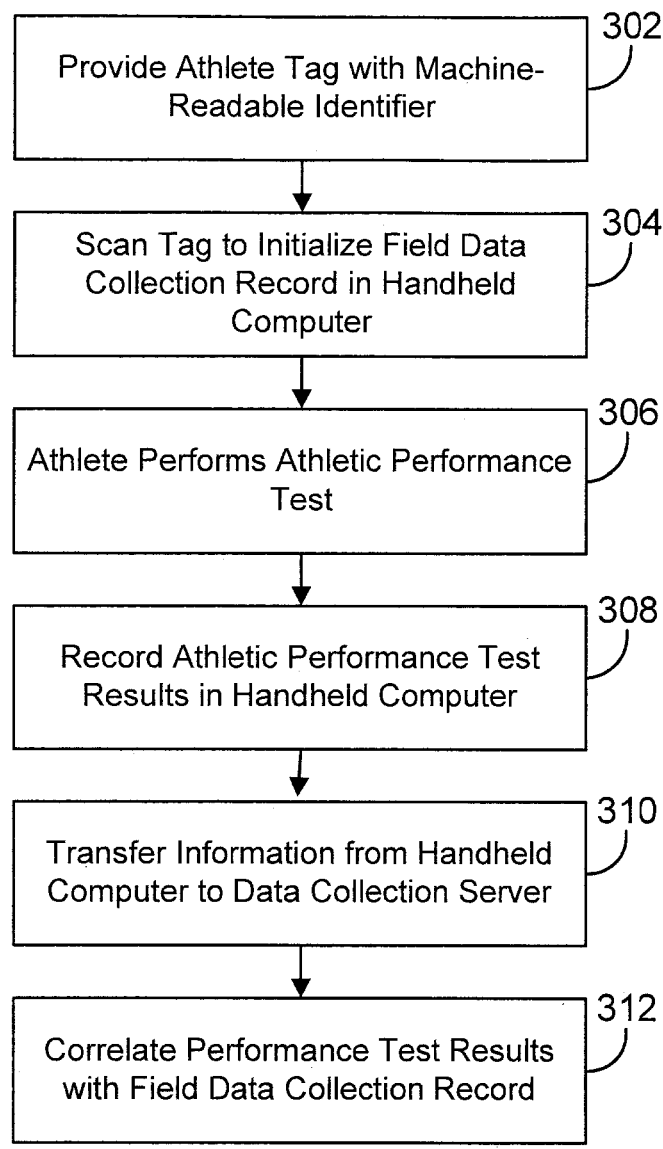
FIG. 3 is a flow diagram of an athletic field data collection method.

FIG. 3 is a flow diagram of an athletic field data collection method 300 that employs athletic field data collection system 110 to collect data on athletic performance from numerous athletes performing a variety of athletic performance tests. For purposes of illustration, data collection method 300 is described with reference to collecting athletic performance data for one of multiple athletes performing athletic performance tests. For example, the athletic performance data could be collected as part of a performance testing event in which athletes participate to obtain an athleticism rating.

In step 302, the athlete is provided a tag with a unique machine-readable identifier. For example, the tag may be a wristband that is worn by the athlete, and the unique machine-readable identifier may be a barcode or a similar identifier that uniquely identifies the athlete during the performance rating event.

In step 304, the identifier on the tag worn by the athlete is scanned at a machine scanner to initialize a field data collection record for the athlete. For example, the identifier is a barcode and it is scanned with the barcode reader 224 of a handheld computer 222 operated by performance testing event worker (e.g., official or volunteer). Additional preliminary identification of the athlete may also be entered as part of initializing the field data collection record for the athlete. For example, a photograph of the athlete may be obtained with the digital camera 226 of handheld device 222. It will be appreciated that such initialization of the field data collection record, entailing scanning of a barcode and taking a digital photograph, allows the performance testing event worker to promptly serve numerous athletes with minimal delay and inconvenience. Other athlete information can also be entered at the time of initialization, such as the athlete height or weight, or any other information about the athlete.

In step 306, the athlete performs an athletic performance test. For example, the athletic performance test may be one of multiple athletic performance tests that form the basis of an athletic performance rating such as a universal and objective athleticism rating system for accurately detecting and recording athletic performance as described in PCT application No. PCT/US2005/040493. The athletic performance tests may relate to general athletic fitness or performance or may relate to a specific sport.

In step 308, the results of an athlete's athletic performance test are recorded. For example, the athletic performance test results are recorded by the performance event testing worker scanning the athlete's barcode tag with the handheld computer 222, accessing the specific performance test from among plural performance tests, and entering the athlete's results for that performance test. Steps 306 and 308 may be repeated for each of the multiple athletic performance tests to be included in the athletic performance rating.

In one implementation, multiple performance test results are temporarily stored in the one or more handheld computer for multiple athletes. There may be one or more handheld computers 222 used at each performance test, or a handheld computer 222 may be used at more than one performance test, depending on the number of athletes participating in the performance testing event.

In step 310, initializing information and performance test results stored in each handheld computer 222 are transferred to data collection server 220. In one implementation, handheld computers 222 communicate with data collection server 220 via extended range local wireless network 223 and transfer batches of performance test results for multiple athletes. It will be appreciated that performance test results could alternatively be transferred as they are entered, but such an implementation would typically draw excessive battery power from handheld computers 222.

In step 312, the performance test results for each athlete are correlated into the field data collection record.

Figure 4:
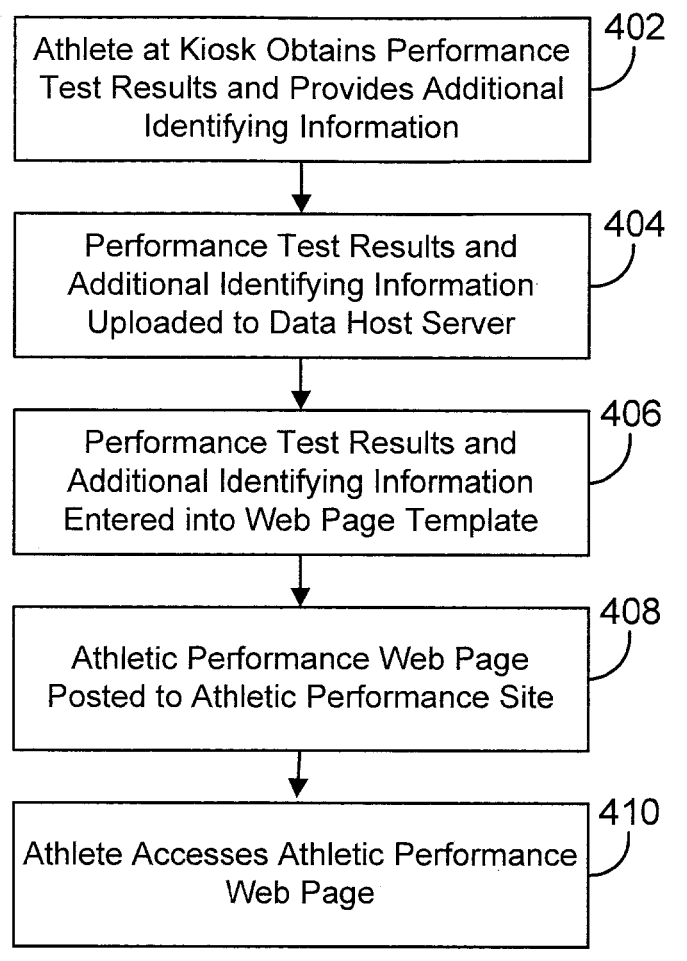
FIG. 4 is a flow diagram of an athletic field data posting method in which athletic performance data are uploaded and posted as athletic performance web pages.

FIG. 4 is a flow diagram of an athletic field data posting method 400 in which athletic performance data collected with athletic field data collection system 110 are uploaded to athletic data host server 130 and posted as athletic performance web pages 150 on athletic performance web site 170. Athletic field data posting method 400 is described with reference to the uploading of data for one athlete, but is similarly applicable to each a multiple athletes participating in a performance testing event.

In step 402, the athlete proceeds to one of kiosks 212 and 214 to obtain a summary of performance test results and to provide additional identifying information. Typically, the athlete proceeds to one of kiosks 212 and 214 upon completion of all of the multiple athletic performance tests required for the athletic performance rating, but completion of all of the athletic performance tests is not required.

For example, at one of kiosks 212 and 214, the athlete has his or her identifying wristband scanned to access athletic performance test results. The athlete is prompted to enter at least his or her name and electronic contact information (e.g., an email address) and is provided a hard copy summary of performance test results, which may include individual performance test results or an athleticism rating, or both. The hard copy summary may also include access information for accessing the personalized athletic performance web page 150 that will be available for the athlete on athletic performance web site 170. The access information may additionally or alternatively be sent to the athlete's email address. The athlete may also be prompted to enter additional information such as his or her height, weight, gender, school or team, primary sport, position, etc.

In step 404, the performance test results and identifying information for each athlete are uploaded from athletic field data collection system 110 athletic data host server 130.

In step 406, the athletic performance test data and the athlete identifying information for each athlete are automatically entered into corresponding fields of a personalized athletic performance web page template 140 to form athletic performance web page 150, which may also include an athleticism rating for the athlete links to sites with training information suited for the performance test results.

In step 408, the athletic performance web page 150 of each athlete is posted to web site 170 and made available over a global computer network (e.g., the Internet).

In step 410, the athlete accesses his or her athletic performance web page 150 to view or modify it. Modification may include, for example, any or all of adding text, music, photos, links, etc.

Figure 5:
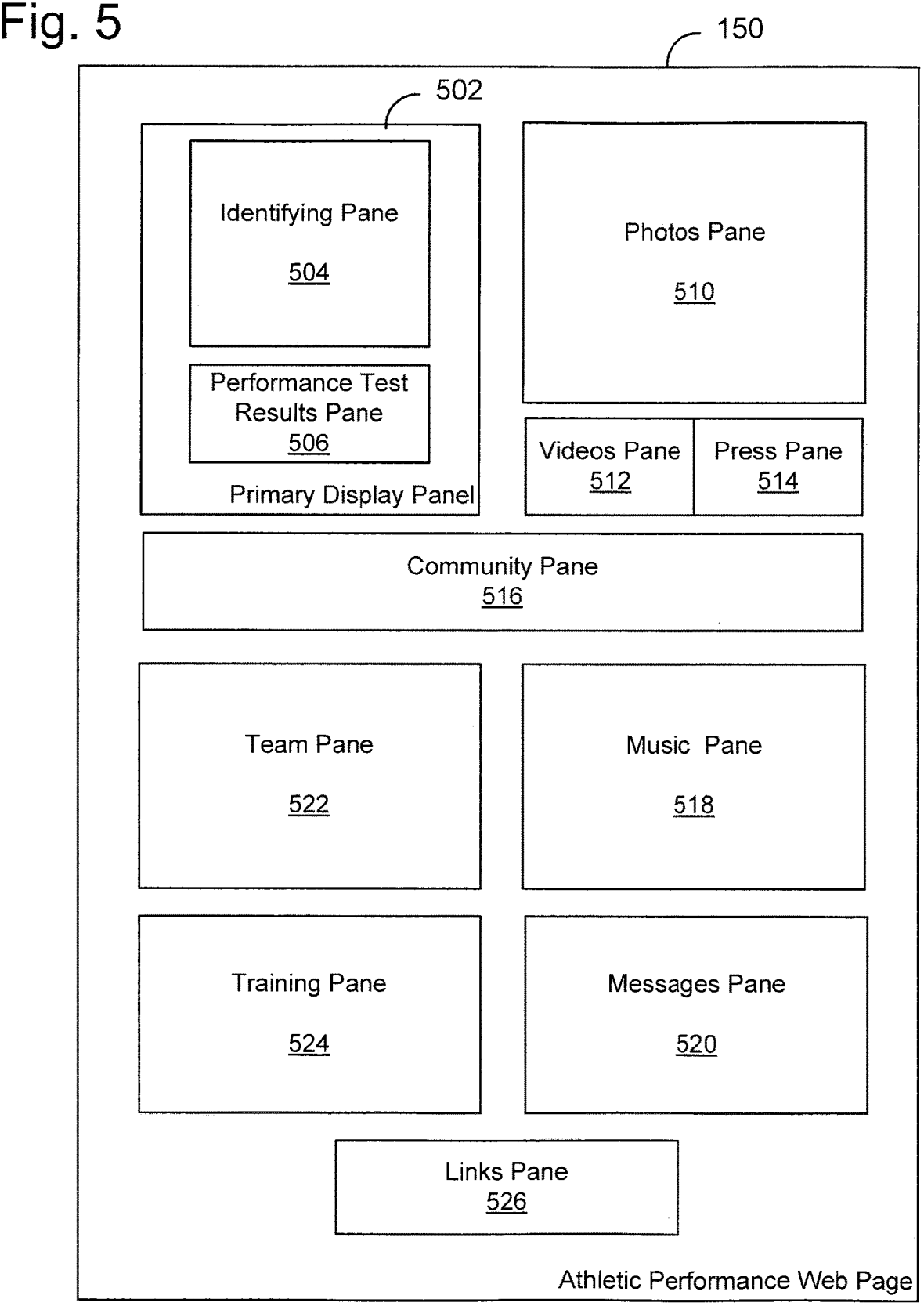
FIG. 5 is a diagrammatic illustration of an exemplary athletic performance web page.

FIG. 5 is a diagrammatic illustration of an exemplary athletic performance web page 150. Athletic performance web page 150 includes plural display panels for displaying various information fields. It will be appreciated that the athletic performance web page 150 of FIG. 5 is merely exemplary and that alternative athletic performance web pages may include any or all of the illustrated display panels or alternative display panels.

Athletic performance web page 150 includes a primary display panel 502 that includes an identifying pane 504 with identifying information about the athlete and a performance test result pane 506. Identifying pane 504 may include identifying information uploaded automatically from athletic field data collection system 110 and additional information later provided by the athlete. The automatically-loaded identifying information may include any or all of the athlete's photograph, name, gender, height, weight, school or team, primary sport, and position. Additional information that may be added by the athlete may include academic performance information, grade point average, college choice, season and career goals, season and career highlights, etc. Performance test result pane 506 displays performance test result information uploaded automatically from athletic field data collection system 110 and may include results of each specific athletic performance test together with a calculated athleticism rating.

Athletic performance web page 150 includes a photos pane 510 for accessing photographs uploaded by the athlete, a videos pane 512 for accessing videos uploaded by the athlete, and press pane 514 for accessing copies of press or news reports uploaded by the athlete. Athletic performance web page 150 may also include a community or "friends" pane 516 for accessing the athletic performance web pages 150 of other athletes who are friends, teammates, etc. of the athlete, a music or tunes pane 518 includes links to music of interest to the athlete, a messages pane 520 includes messages posted by visitors to the web page 150, a team pane 522 includes information or links relating to the athlete's team, a training pane 524 includes one or more links to training information suited for the athlete, and a links pane 526 includes links to other internet sites of interest to the athlete.

The training information suited for the athlete available from training pane 524 can be provided by the operator of web site 170 based upon the athlete's performance test results or athleticism rating. In this regard, the training information functions more as a training aid for the athlete than as information about the athlete or his or her interests. For example, the training information may include specific proposed exercises or drills based upon specific performance test results.

In addition to athletic performance web pages 150 for individual athletes, athletic performance web site 170 may also include one or more indices, summaries or search pages by which an athlete's personalized web page could be accessed. The search fields may relate to any of the information fields included in the athletic performance web pages 150 including, but not limited to, athlete name, school name, sport, position, athleticism rating, height, weight, etc. Search results may be listed as according to selected rank criteria, such as performance test results or athleticism ratings, and may be simple text lists or thumbnail representations of the athletic performance web pages 150. As a result, athlete's can see how they or their teams rate or rank relative to other athletes and teams on a local, state, or national basis.

The present invention provides an integrated information system for athletes that incorporates athlete event registration, field data collection, performance evaluation and ranking, and personal profile creation. The system provides efficient, wireless handling of field event data and the posting of results in profiles that are accessible and searchable. Automatic generation of athletic performance web pages 150, together with their being customizable by the athletes, provides athletes with performance information and an environment for social interaction with other athletes having similar interests and goals.

In view of the many possible embodiments to which the principles of our invention may be applied, it should be recognized that the detailed embodiments are illustrative only and should not be taken as limiting the scope of our invention. Rather, the invention includes all such embodiments as may come within the scope and spirit of the following claims and equivalents thereto.

We claim:

1. A system comprising:
an athletic data collection system, wherein the athletic data collection system comprises a non-transitory computer-readable medium storing computer-executable instructions that, when executed by a processor of the athletic data collection system, perform at least:
automatically receiving, directly from an athletic device worn by an athlete, athletic performance data of the athlete performing in an athletic event;
automatically associating athlete identifying information for the athlete with the athletic performance data; and
in response to receiving the athletic identifying information and the athletic performance data, transmitting electronic signals comprising instructions configured to automatically generate a personalized athletic performance web site for each of the athlete, each of the personalized athletic performance web sites comprising:
an identifying section configured to display at least a portion of identifying information of the athlete; and
a performance test result section configured to display performance test data received from the athletic event,
wherein integrity of the personalized athletic performance web site is improved due to the athletic data collection system directly, without any manual handling, receiving athletic performance data collected by the athletic device.

2. The system of claim 1, wherein the athlete's performance data is entirely collected from the athletic device.

3. The system of claim 2, wherein the athletic event is team-based sporting event.

4. The system of claim 1, wherein the non-transitory computer-readable medium further stores computer-executable instructions that, when executed by a processor, further causes at least:
automatically calculating, based on the received athletic performance data, an athleticism rating for the athlete; and
transmitting electronic instructions, that when executed by a processor, are configured to display the athleticism rating of the athlete on their respective web site.

5. The system of claim 1, wherein at least a portion of the athletic performance data collected from the athletic device was previously obtained by an external device in electronic communication with the athletic device during the athletic event.

6. The system of claim 1, wherein the athletic data collection system comprises:
an electronic device configured to receive the athletic performance data from the athletic device via a wireless communication pathway.

7. The system of claim 1, wherein the personalized athletic performance web site for the athlete is modifiable by the athlete.

8. The system of claim 1, wherein the personalized athletic performance web site includes access to training information adapted to the athlete according to the athletic performance data of the athlete.

9. The system of claim 1, wherein the athletic device is configured to transmit the athletic performance data via a wireless communication pathway.

10. The system of claim 4, wherein the athletic event is a collection of sport-specific performance tests.

11. The system of claim 10, wherein the athleticism rating is a sport-specific athletic rating.

12. The system of claim 10, wherein the non-transitory computer-readable medium further stores computer-executable instructions that, when executed by a processor, further cause at least:
receiving a query to sort athletic data of a plurality of automatically generated web sites comprising at least the web_site of the athlete; and
determining a ranking of the plurality of web sites responsive to the query.

13. The system of claim 12, wherein the ranking of the plurality of web sites is based on the athletic rating.

14. A computerized method that improves integrity of athleticism ratings of athletes comprising:
automatically wirelessly receiving, from a portable computer located in an athletic device of an athlete, directly at an athletic data collection system, athletic performance data collected by the athletic device, collected from the athlete's performance in an athletic event;
in response to receiving athletic identifying information of the athletic performance data, automatically generating, by the athletic data collection system, a personalized athletic performance web site for the athlete, the personalized athletic performance web site comprising:
an identifying section configured to display at least a portion of identifying information of the athlete;
a performance test result section configured to display performance test data received at the athletic data collection system; and
an automatically calculated athleticism rating based on at least a portion of the received athletic performance data,
wherein the integrity of the automatically calculated athleticism rating is improved due to the athletic data collection system directly, without any manual handling, receiving athletic performance data collected by the athletic device.

15. The method of claim 14, wherein at least a portion of the athlete's athletic performance data is collected from a portable computer.

16. The method of claim 14, wherein the athletic event is team-based sporting event.

17. The method of claim 15, wherein at least a portion of the athletic performance data collected from the portable computer was previously obtained by an external device in electronic communication with the portable computer during the athletic event.

18. The method of claim 14, wherein the athletic event is a collection of sport-specific performance tests.

19. The method of claim 18, wherein the athletic rating is a sport-specific athletic rating.

20. The method of claim 19, further comprising:
receiving a query to sort athletic data of a plurality of automatically generated web_sites comprising at least the web_site of the athlete; and
ranking the plurality of web_sites responsive to the query.

* * * * *